(12) United States Patent
Medan et al.

(10) Patent No.: US 9,412,357 B2
(45) Date of Patent: *Aug. 9, 2016

(54) MAPPING ULTRASOUND TRANSDUCERS

(71) Applicants: Yoav Medan, Haifa (IL); Yoni Hertzberg, Moshav (IL); Dov Maor, Haifa (IL)

(72) Inventors: Yoav Medan, Haifa (IL); Yoni Hertzberg, Moshav (IL); Dov Maor, Haifa (IL)

(73) Assignee: INSIGHTEC LTD., Tirat Carmel (IL)

( * ) Notice: Subject to any disclaimer, the term of this patent is extended or adjusted under 35 U.S.C. 154(b) by 233 days.

This patent is subject to a terminal disclaimer.

(21) Appl. No.: 14/138,864

(22) Filed: Dec. 23, 2013

(65) Prior Publication Data

US 2014/0112095 A1    Apr. 24, 2014

Related U.S. Application Data

(62) Division of application No. 12/904,655, filed on Oct. 14, 2010, now Pat. No. 8,661,873.

(60) Provisional application No. 61/251,450, filed on Oct. 14, 2009.

(51) Int. Cl.
*G10K 11/34* (2006.01)
*A61B 8/00* (2006.01)
*A61N 7/00* (2006.01)
(Continued)

(52) U.S. Cl.
CPC .............. *G10K 11/346* (2013.01); *A61B 8/587* (2013.01); *A61N 2007/0078* (2013.01); *A61N 2007/0095* (2013.01); *G01H 17/00* (2013.01); *G01N 29/30* (2013.01)

(58) Field of Classification Search
CPC ................. A61B 8/587; G10K 11/346; A61N 2007/0078; A61N 2007/0095; G01H 17/00; G01N 29/30; G01S 15/8934–15/8947
USPC .......... 73/1.82, 1.86, 584; 600/437, 448, 459; 324/307; 367/13
See application file for complete search history.

(56) References Cited

U.S. PATENT DOCUMENTS 2,795,709 A    6/1957   Camp
3,142,035 A    7/1964   Harris
(Continued)

FOREIGN PATENT DOCUMENTS

CN    1744861 A    3/2006
CN    1981708 A    6/2007
(Continued)

OTHER PUBLICATIONS

Examination Report Received for European Patent Application No. 05773991.4, mailed on Nov. 2, 2012, 5 pages.
(Continued)

*Primary Examiner* — Peter Macchiarolo
*Assistant Examiner* — David L Singer
(74) *Attorney, Agent, or Firm* — Morgan, Lewis & Bockius LLP (57) ABSTRACT

Ultrasound transducers may be mapped by varying a focus-affecting parameter and adjusting the parameter so as to improve focus quality. In some embodiments, mapping involves successively varying the phase of one transducer element, or group of elements, with respect to a constant phase of the other transducer elements, and determining the phase at which a tissue displacement in the ultrasound focus is maximized.

20 Claims, 5 Drawing Sheets

(51) Int. Cl.
*G01H 17/00* (2006.01)
*G01N 29/30* (2006.01)

(56) References Cited

U.S. PATENT DOCUMENTS

| | | |
|---|---|---|
| 3,559,159 A | 1/1971 | Harms et al. |
| 3,942,150 A | 3/1976 | Booth et al. |
| 3,974,475 A | 8/1976 | Burckhardt et al. |
| 3,992,693 A | 11/1976 | Martin et al. |
| 4,000,493 A | 12/1976 | Spaulding et al. |
| 4,052,723 A | 10/1977 | Miller |
| 4,074,564 A | 2/1978 | Anderson |
| 4,206,653 A | 6/1980 | Lemay |
| 4,211,132 A | 7/1980 | Nichols, III et al. |
| 4,221,132 A | 9/1980 | Poole |
| 4,307,613 A | 12/1981 | Fox |
| 4,339,952 A | 7/1982 | Foster |
| 4,441,486 A | 4/1984 | Pounds |
| 4,454,597 A | 6/1984 | Sullivan |
| 4,478,083 A | 10/1984 | Hassler et al. |
| 4,505,156 A | 3/1985 | Questo |
| 4,526,168 A | 7/1985 | Hassler et al. |
| 4,537,074 A | 8/1985 | Dietz |
| 4,549,533 A | 10/1985 | Cain et al. |
| 4,554,925 A | 11/1985 | Young |
| 4,586,512 A | 5/1986 | Do-huu et al. |
| 4,616,231 A | 10/1986 | Autrey et al. |
| 4,636,964 A | 1/1987 | Jacobs et al. |
| 4,646,756 A | 3/1987 | Watmough et al. |
| 4,647,808 A | 3/1987 | Shibuya |
| 4,662,222 A | 5/1987 | Johnson |
| 4,757,820 A | 7/1988 | Itoh |
| 4,817,614 A | 4/1989 | Hassler et al. |
| 4,823,053 A | 4/1989 | Mccracken et al. |
| 4,858,597 A | 8/1989 | Kurtze et al. |
| 4,858,613 A | 8/1989 | Fry et al. |
| 4,865,042 A | 9/1989 | Umemura et al. |
| 4,886,491 A | 12/1989 | Parisi et al. |
| 4,888,746 A | 12/1989 | Wurster et al. |
| 4,889,122 A | 12/1989 | Watmough et al. |
| 4,893,284 A | 1/1990 | Magrane |
| 4,893,624 A | 1/1990 | Lele |
| 4,937,767 A | 6/1990 | Reuschel et al. |
| 4,938,217 A | 7/1990 | Lele |
| 4,957,099 A | 9/1990 | Hassler |
| 4,989,143 A * | 1/1991 | O'Donnell .............. G01H 17/00 600/437 |
| 5,015,929 A | 5/1991 | Cathignol et al. |
| 5,143,063 A | 9/1992 | Fellner |
| 5,165,412 A | 11/1992 | Okazaki |
| 5,172,343 A | 12/1992 | O'Donnell |
| 5,186,175 A | 2/1993 | Hirama et al. |
| 5,197,475 A | 3/1993 | Antich et al. |
| 5,209,221 A | 5/1993 | Riedlinger |
| 5,211,160 A | 5/1993 | Talish et al. |
| 5,247,935 A | 9/1993 | Cline et al. |
| 5,266,863 A | 11/1993 | Nonami et al. |
| 5,267,221 A | 11/1993 | Miller et al. |
| 5,269,307 A | 12/1993 | Fife et al. |
| 5,271,400 A | 12/1993 | Dumoulin et al. |
| 5,275,165 A | 1/1994 | Ettinger et al. |
| 5,291,890 A | 3/1994 | Cline et al. |
| 5,305,737 A | 4/1994 | Vago |
| 5,307,812 A | 5/1994 | Hardy et al. |
| 5,307,816 A | 5/1994 | Hashimoto et al. |
| 5,318,025 A | 6/1994 | Dumoulin et al. |
| 5,323,779 A | 6/1994 | Hardy et al. |
| 5,327,884 A | 7/1994 | Hardy et al. |
| 5,329,930 A | 7/1994 | Thomas, III et al. |
| 5,368,031 A | 11/1994 | Cline et al. |
| 5,368,032 A | 11/1994 | Cline et al. |
| 5,379,642 A | 1/1995 | Reckwerdt et al. |
| 5,388,461 A | 2/1995 | Rigby |
| 5,391,140 A | 2/1995 | Schaetzle et al. |
| 5,413,550 A | 5/1995 | Castel |
| 5,419,761 A | 5/1995 | Narayanan et al. |
| 5,435,312 A | 7/1995 | Spivey et al. |
| 5,443,068 A | 8/1995 | Cline et al. |
| 5,474,071 A | 12/1995 | Chapelon et al. |
| 5,477,736 A | 12/1995 | Lorraine |
| 5,485,839 A | 1/1996 | Aida et al. |
| 5,490,512 A | 2/1996 | Kwon et al. |
| 5,490,840 A | 2/1996 | Uzgiris et al. |
| 5,507,790 A | 4/1996 | Weiss |
| 5,514,086 A | 5/1996 | Parisi et al. |
| 5,520,186 A | 5/1996 | Deitrich |
| 5,520,188 A | 5/1996 | Hennige et al. |
| 5,520,612 A | 5/1996 | Winder et al. |
| 5,526,814 A | 6/1996 | Cline et al. |
| 5,527,273 A | 6/1996 | Manna et al. |
| 5,546,360 A | 8/1996 | Deegan |
| 5,549,638 A | 8/1996 | Burdette |
| 5,553,618 A | 9/1996 | Suzuki et al. |
| 5,573,497 A | 11/1996 | Chapelon |
| 5,582,578 A | 12/1996 | Zhong et al. |
| 5,590,653 A | 1/1997 | Aida et al. |
| 5,590,657 A | 1/1997 | Cain et al. |
| 5,601,526 A | 2/1997 | Chapelon et al. |
| 5,605,154 A | 2/1997 | Ries et al. |
| 5,606,971 A | 3/1997 | Sarvazyan |
| 5,617,371 A | 4/1997 | Williams |
| 5,617,857 A | 4/1997 | Chader et al. |
| 5,643,179 A | 7/1997 | Fujimoto |
| 5,662,170 A | 9/1997 | Donovan et al. |
| 5,665,054 A | 9/1997 | Dory |
| 5,666,954 A | 9/1997 | Chapelon et al. |
| 5,676,673 A | 10/1997 | Ferre et al. |
| 5,687,729 A | 11/1997 | Schaetzle |
| 5,694,936 A | 12/1997 | Fujimoto et al. |
| 5,711,300 A | 1/1998 | Schneider et al. |
| 5,718,226 A | 2/1998 | Riza |
| 5,722,411 A | 3/1998 | Suzuki et al. |
| 5,725,482 A | 3/1998 | Bishop |
| 5,728,062 A | 3/1998 | Brisken |
| 5,739,625 A | 4/1998 | Falcus |
| 5,743,863 A | 4/1998 | Chapelon |
| 5,752,515 A | 5/1998 | Jolesz et al. |
| 5,759,162 A | 6/1998 | Oppelt et al. |
| 5,762,616 A | 6/1998 | Talish |
| 5,769,790 A | 6/1998 | Watkins et al. |
| 5,769,879 A | 6/1998 | Richards et al. |
| 5,784,336 A | 7/1998 | Gopinathan et al. |
| 5,810,008 A | 9/1998 | Dekel et al. |
| 5,810,731 A | 9/1998 | Sarvazyan et al. |
| 5,817,021 A | 10/1998 | Reichenberger |
| 5,817,036 A | 10/1998 | Anthony et al. |
| 5,823,990 A | 10/1998 | Henley |
| 5,827,204 A | 10/1998 | Grandia et al. |
| 5,873,845 A | 2/1999 | Cline et al. |
| 5,884,631 A | 3/1999 | Silberg |
| 5,885,211 A | 3/1999 | Eppstein et al. |
| 5,891,040 A | 4/1999 | Grenon et al. |
| 5,897,495 A | 4/1999 | Aida et al. |
| 5,904,659 A | 5/1999 | Duarte et al. |
| 5,922,962 A | 7/1999 | Ishrak et al. |
| 5,938,600 A | 8/1999 | Van Vaals et al. |
| 5,938,608 A | 8/1999 | Bieger et al. |
| 5,947,900 A | 9/1999 | Derbyshire et al. |
| 5,984,881 A | 11/1999 | Ishibashi et al. |
| 6,004,269 A | 12/1999 | Crowley et al. |
| 6,007,499 A | 12/1999 | Martin et al. |
| 6,013,048 A | 1/2000 | Podany et al. |
| 6,023,636 A | 2/2000 | Wendt et al. |
| 6,032,675 A | 3/2000 | Rubinsky |
| 6,033,375 A | 3/2000 | Brumbach |
| 6,036,644 A | 3/2000 | Schutt |
| 6,039,048 A | 3/2000 | Silberg |
| 6,042,556 A | 3/2000 | Beach et al. |
| 6,045,777 A | 4/2000 | Church et al. |
| 6,071,239 A | 6/2000 | Cribbs et al. |
| 6,088,295 A | 7/2000 | Altes |
| 6,106,511 A | 8/2000 | Jensen |
| 6,113,558 A | 9/2000 | Rosenschein et al. |
| 6,113,559 A | 9/2000 | Klopotek |

(56) References Cited

U.S. PATENT DOCUMENTS

| | | | |
|---|---|---|---|
| 6,128,522 A | 10/2000 | Acker et al. | |
| 6,128,958 A | 10/2000 | Cain | |
| 6,135,960 A | 10/2000 | Holmberg | |
| 6,135,971 A | 10/2000 | Hutchinson et al. | |
| 6,142,939 A | 11/2000 | Eppstein et al. | |
| 6,156,549 A | 12/2000 | Drewes et al. | |
| 6,193,659 B1 | 2/2001 | Ramamurthy et al. | |
| 6,217,530 B1 | 4/2001 | Martin et al. | |
| 6,242,915 B1 | 6/2001 | Hurd | |
| 6,246,895 B1* | 6/2001 | Plewes | A61B 8/00 324/309 |
| 6,246,896 B1 | 6/2001 | Dumoulin et al. | |
| 6,263,230 B1 | 7/2001 | Haynor et al. | |
| 6,267,734 B1 | 7/2001 | Ishibashi et al. | |
| 6,289,233 B1 | 9/2001 | Dumoulin et al. | |
| 6,309,355 B1 | 10/2001 | Cain et al. | |
| 6,317,619 B1 | 11/2001 | Boernert et al. | |
| 6,322,527 B1 | 11/2001 | Talish | |
| 6,334,846 B1 | 1/2002 | Ishibashi et al. | |
| 6,350,245 B1 | 2/2002 | Cimino | |
| 6,374,132 B1 | 4/2002 | Acker et al. | |
| 6,392,330 B1 | 5/2002 | Zloter et al. | |
| 6,397,094 B1 | 5/2002 | Ludeke et al. | |
| 6,413,216 B1 | 7/2002 | Cain et al. | |
| 6,419,648 B1 | 7/2002 | Vitek et al. | |
| 6,424,597 B1 | 7/2002 | Bolomey et al. | |
| 6,425,867 B1 | 7/2002 | Vaezy et al. | |
| 6,428,477 B1 | 8/2002 | Mason | |
| 6,428,532 B1 | 8/2002 | Doukas et al. | |
| 6,433,464 B2 | 8/2002 | Jones | |
| 6,461,314 B1 | 10/2002 | Pant et al. | |
| 6,475,150 B2 | 11/2002 | Haddad | |
| 6,478,739 B1 | 11/2002 | Hong | |
| 6,503,204 B1 | 1/2003 | Sumanaweera et al. | |
| 6,506,154 B1 | 1/2003 | Ezion et al. | |
| 6,506,171 B1* | 1/2003 | Vitek | A61H 23/0245 600/439 |
| 6,508,774 B1 | 1/2003 | Acker et al. | |
| 6,511,064 B1 | 1/2003 | Phinney et al. | |
| 6,511,428 B1 | 1/2003 | Azuma et al. | |
| 6,522,142 B1 | 2/2003 | Freundlich | |
| 6,523,272 B1 | 2/2003 | Morales | |
| 6,524,251 B2 | 2/2003 | Rabiner et al. | |
| 6,543,272 B1 | 4/2003 | Vitek | |
| 6,554,826 B1 | 4/2003 | Deardorff | |
| 6,559,644 B2 | 5/2003 | Froundlich et al. | |
| 6,566,878 B1 | 5/2003 | Komura et al. | |
| 6,582,381 B1 | 6/2003 | Yehezkeli et al. | |
| 6,589,174 B1 | 7/2003 | Chopra et al. | |
| 6,599,256 B1 | 7/2003 | Acker et al. | |
| 6,612,988 B2 | 9/2003 | Maor et al. | |
| 6,613,004 B1 | 9/2003 | Vitek et al. | |
| 6,613,005 B1* | 9/2003 | Friedman | A61N 7/02 600/371 |
| 6,618,608 B1 | 9/2003 | Watkins et al. | |
| 6,618,620 B1 | 9/2003 | Freundlich et al. | |
| 6,626,854 B2 | 9/2003 | Friedman et al. | |
| 6,626,855 B1 | 9/2003 | Weng et al. | |
| 6,629,929 B1 | 10/2003 | Jago et al. | |
| 6,645,162 B2 | 11/2003 | Friedman et al. | |
| 6,652,461 B1 | 11/2003 | Levkovitz et al. | |
| 6,666,833 B1 | 12/2003 | Friedman et al. | |
| 6,676,601 B1 | 1/2004 | Lacoste et al. | |
| 6,676,602 B1 | 1/2004 | Barnes et al. | |
| 6,679,855 B2 | 1/2004 | Horn et al. | |
| 6,705,994 B2 | 3/2004 | Vortman et al. | |
| 6,719,694 B2 | 4/2004 | Weng et al. | |
| 6,733,450 B1 | 5/2004 | Alexandrov et al. | |
| 6,735,461 B2 | 5/2004 | Vitek et al. | |
| 6,761,691 B2 | 7/2004 | Tsuzuki | |
| 6,770,031 B2 | 8/2004 | Hynynen et al. | |
| 6,770,039 B2 | 8/2004 | Zhong et al. | |
| 6,788,619 B2 | 9/2004 | Calvert | |
| 6,790,180 B2 | 9/2004 | Vitek | |
| 6,805,129 B1 | 10/2004 | Pless et al. | |
| 6,824,516 B2 | 11/2004 | Batten et al. | |
| 6,936,046 B2 | 8/2005 | Hissong et al. | |
| 6,951,540 B2 | 10/2005 | Ebbini et al. | |
| 6,961,606 B2 | 11/2005 | DeSilets et al. | |
| 7,001,379 B2 | 2/2006 | Behl et al. | |
| 7,077,820 B1 | 7/2006 | Kadziauskas et al. | |
| 7,094,205 B2 | 8/2006 | Marmarelis | |
| 7,128,711 B2 | 10/2006 | Medan et al. | |
| 7,155,271 B2 | 12/2006 | Halperin et al. | |
| 7,175,596 B2 | 2/2007 | Vitek et al. | |
| 7,175,599 B2 | 2/2007 | Hynynen et al. | |
| 7,264,592 B2 | 9/2007 | Shehada | |
| 7,264,597 B2 | 9/2007 | Cathignol | |
| 7,267,650 B2 | 9/2007 | Chow et al. | |
| 7,344,509 B2 | 3/2008 | Hynynen et al. | |
| 7,377,900 B2 | 5/2008 | Vitek et al. | |
| 7,429,248 B1 | 9/2008 | Winder et al. | |
| 7,452,357 B2 | 11/2008 | Vlegele et al. | |
| 7,505,805 B2 | 3/2009 | Kuroda | |
| 7,505,808 B2 | 3/2009 | Anderson et al. | |
| 7,507,213 B2 | 3/2009 | Schultheiss et al. | |
| 7,510,536 B2 | 3/2009 | Foley et al. | |
| 7,511,501 B2 | 3/2009 | Wexler | |
| 7,535,794 B2 | 5/2009 | Prus et al. | |
| 7,553,284 B2 | 6/2009 | Vaitekunas | |
| 7,603,162 B2 | 10/2009 | Danz et al. | |
| 7,611,462 B2 | 11/2009 | Vortman et al. | |
| 7,652,410 B2 | 1/2010 | Prus | |
| 7,699,780 B2 | 4/2010 | Vitek et al. | |
| 7,819,805 B2 | 10/2010 | Davies et al. | |
| 1,006,603 A1 | 3/2011 | Vitek et al. | |
| 8,057,408 B2 | 11/2011 | Cain et al. | |
| 8,075,488 B2 | 12/2011 | Burton | |
| 8,661,873 B2 | 3/2014 | Medan et al. | |
| 8,932,237 B2 | 1/2015 | Vitek et al. | |
| 2001/0031922 A1 | 10/2001 | Weng et al. | |
| 2002/0016557 A1 | 2/2002 | Duarte et al. | |
| 2002/0035779 A1 | 3/2002 | Krieg et al. | |
| 2002/0082528 A1 | 6/2002 | Friedman et al. | |
| 2002/0082589 A1 | 6/2002 | Friedman et al. | |
| 2002/0095087 A1 | 7/2002 | Mourad et al. | |
| 2002/0111552 A1 | 8/2002 | Maor et al. | |
| 2002/0151790 A1 | 10/2002 | Abend | |
| 2002/0161300 A1 | 10/2002 | Hoff et al. | |
| 2002/0188229 A1 | 12/2002 | Ryaby | |
| 2003/0004439 A1 | 1/2003 | Pant et al. | |
| 2003/0055308 A1 | 3/2003 | Friemel et al. | |
| 2003/0060820 A1 | 3/2003 | Maguire et al. | |
| 2003/0187371 A1 | 10/2003 | Vortman et al. | |
| 2004/0030251 A1 | 2/2004 | Ebbini et al. | |
| 2004/0059265 A1 | 3/2004 | Candy et al. | |
| 2004/0068186 A1 | 4/2004 | Ishida et al. | |
| 2004/0082868 A1 | 4/2004 | Campbell et al. | |
| 2004/0116809 A1 | 6/2004 | Chow et al. | |
| 2004/0122316 A1 | 6/2004 | Satoh | |
| 2004/0122323 A1 | 6/2004 | Vortman et al. | |
| 2004/0143187 A1 | 7/2004 | Biagi et al. | |
| 2004/0147919 A1 | 7/2004 | Behl et al. | |
| 2004/0210134 A1 | 10/2004 | Hynynen et al. | |
| 2004/0210135 A1 | 10/2004 | Hynynen et al. | |
| 2004/0236253 A1 | 11/2004 | Vortman et al. | |
| 2004/0236523 A1 | 11/2004 | Taylor | |
| 2004/0267126 A1 | 12/2004 | Takeuchi | |
| 2005/0033201 A1 | 2/2005 | Takahashi et al. | |
| 2005/0096542 A1 | 5/2005 | Weng et al. | |
| 2005/0131301 A1 | 6/2005 | Peszynski et al. | |
| 2005/0154304 A1 | 7/2005 | Robinson | |
| 2005/0199058 A1 | 9/2005 | Danz et al. | |
| 2005/0203444 A1 | 9/2005 | Schonenberger et al. | |
| 2005/0240126 A1 | 10/2005 | Foley et al. | |
| 2005/0251046 A1 | 11/2005 | Yamamoto et al. | |
| 2006/0052661 A1 | 3/2006 | Gannot et al. | |
| 2006/0052701 A1 | 3/2006 | Carter et al. | |
| 2006/0052706 A1 | 3/2006 | Hynynen et al. | |
| 2006/0058671 A1* | 3/2006 | Vitek | A61N 7/02 600/447 |
| 2006/0058678 A1 | 3/2006 | Vitek et al. | |
| 2006/0106300 A1 | 5/2006 | Seppenwoolde et al. | |
| 2006/0173307 A1 | 8/2006 | Amara et al. | |

(56) References Cited

U.S. PATENT DOCUMENTS

| | | |
|---|---|---|
| 2006/0173321 A1 | 8/2006 | Kubota et al. |
| 2006/0173385 A1 | 8/2006 | Lidgren et al. |
| 2006/0184034 A1 | 8/2006 | Haim et al. |
| 2006/0184069 A1 | 8/2006 | Vaitekunas |
| 2006/0206105 A1 | 9/2006 | Chopra et al. |
| 2006/0229594 A1 | 10/2006 | Francischelli et al. |
| 2006/0235302 A1 | 10/2006 | Grossman et al. |
| 2006/0253026 A1 | 11/2006 | Gueck et al. |
| 2007/0016039 A1 | 1/2007 | Vortman et al. |
| 2007/0055140 A1 | 3/2007 | Kuroda |
| 2007/0066897 A1 | 3/2007 | Sekins et al. |
| 2007/0073135 A1 | 3/2007 | Lee et al. |
| 2007/0098232 A1 | 5/2007 | Matula et al. |
| 2007/0167781 A1 | 7/2007 | Vortman et al. |
| 2007/0167798 A1 | 7/2007 | Cai et al. |
| 2007/0197918 A1 | 8/2007 | Vitek et al. |
| 2007/0219470 A1 | 9/2007 | Talish et al. |
| 2007/0239062 A1 | 10/2007 | Chopra et al. |
| 2007/0265560 A1 | 11/2007 | Soltani et al. |
| 2007/0276237 A1 | 11/2007 | Li |
| 2008/0027342 A1 | 1/2008 | Rouw et al. |
| 2008/0030104 A1 | 2/2008 | Prus |
| 2008/0031090 A1 | 2/2008 | Prus et al. |
| 2008/0033278 A1 | 2/2008 | Assif |
| 2008/0082026 A1 | 4/2008 | Schmidt et al. |
| 2008/0103558 A1 | 5/2008 | Wenzel et al. |
| 2008/0108900 A1 | 5/2008 | Lee et al. |
| 2008/0125660 A1 | 5/2008 | Yao et al. |
| 2008/0183077 A1 | 7/2008 | Moreau-Gobard et al. |
| 2008/0228081 A1 | 9/2008 | Becker et al. |
| 2008/0312562 A1 | 12/2008 | Routh et al. |
| 2009/0088623 A1 | 4/2009 | Vortman et al. |
| 2009/0093721 A1 | 4/2009 | Katsuyama |
| 2009/0096450 A1 | 4/2009 | Roland |
| 2009/0118619 A1 | 5/2009 | Oshiki |
| 2009/0230823 A1* | 9/2009 | Kushculey .............. A61N 7/02 310/366 |
| 2010/0030076 A1 | 2/2010 | Vortman et al. |
| 2010/0056962 A1 | 3/2010 | Vortman et al. |
| 2010/0125193 A1 | 5/2010 | Zadicario |
| 2010/0179425 A1 | 7/2010 | Zadicario |
| 2010/0268088 A1 | 10/2010 | Prus et al. |
| 2010/0274130 A1 | 10/2010 | Anand et al. |
| 2010/0318002 A1 | 12/2010 | Prus et al. |
| 2011/0034800 A1* | 2/2011 | Vitek ................... A61B 5/055 600/411 |
| 2011/0094288 A1 | 4/2011 | Medan et al. |
| 2011/0130663 A1 | 6/2011 | Raju et al. |
| 2011/0137147 A1 | 6/2011 | Skliar et al. |
| 2011/0251527 A1 | 10/2011 | Kushculey et al. |
| 2011/0270136 A1 | 11/2011 | Vitek et al. |
| 2012/0083695 A1 | 4/2012 | Napolitano et al. |
| 2013/0077441 A1 | 3/2013 | Ramamurthy et al. |

FOREIGN PATENT DOCUMENTS

| | | | |
|---|---|---|---|
| CN | 101137329 A | | 3/2008 |
| CN | 102348481 A | | 2/2012 |
| CN | 102946945 A | | 2/2013 |
| CN | 103140261 A | | 6/2013 |
| DE | 10102317 A1 | | 8/2002 |
| EP | 0031614 A1 | | 7/1981 |
| EP | 174920 A1 | | 3/1986 |
| EP | 272347 A1 | | 6/1988 |
| EP | 0320303 | | 6/1989 |
| EP | 450334 A2 | | 10/1991 |
| EP | 462311 A1 | | 12/1991 |
| EP | 467690 A2 | | 1/1992 |
| EP | 0558029 | | 9/1993 |
| EP | 627206 A2 | | 12/1994 |
| EP | 734742 A2 | | 10/1996 |
| EP | 875203 A2 | | 11/1998 |
| EP | 1582886 A1 | | 10/2005 |
| EP | 1591073 A1 | | 11/2005 |
| EP | 1774920 | | 4/2007 |
| EP | 1936404 | | 6/2008 |
| EP | 2429656 B1 | | 6/2013 |
| EP | 2563475 B1 | | 8/2014 |
| FR | 2692999 A1 | | 12/1993 |
| FR | 280661 1 | | 9/2001 |
| GB | 2019565 A | | 10/1979 |
| JP | 07/184907 | | 7/1995 |
| JP | 00/166940 | | 6/2000 |
| JP | 01/516075 | | 9/2001 |
| JP | 02/530145 | | 9/2002 |
| JP | 2006-203653 T | | 2/2006 |
| JP | 5066569 B2 | | 11/2012 |
| JP | 5087007 B2 | | 11/2012 |
| WO | 91/15999 A1 | | 10/1991 |
| WO | 91/19332 A1 | | 12/1991 |
| WO | WO-93/15415 A1 | | 8/1993 |
| WO | WO-95/14505 | | 6/1995 |
| WO | WO-97/17018 A1 | | 5/1997 |
| WO | 00/78232 A1 | | 12/2000 |
| WO | 01/43640 A2 | | 6/2001 |
| WO | 01/80708 A2 | | 11/2001 |
| WO | WO-01/80709 | | 11/2001 |
| WO | 01/80708 A3 | | 3/2002 |
| WO | WO-02/44753 | | 6/2002 |
| WO | WO-03/013654 | | 2/2003 |
| WO | 03/070105 A1 | | 8/2003 |
| WO | WO-2004/021044 A1 | | 3/2004 |
| WO | 2004/066856 A1 | | 8/2004 |
| WO | WO-2005/038745 | | 4/2005 |
| WO | 2005/058029 A2 | | 6/2005 |
| WO | 2006/018686 A1 | | 2/2006 |
| WO | 2006/021851 A1 | | 3/2006 |
| WO | WO-2006/025001 A1 | | 3/2006 |
| WO | WO-2007/051066 | | 5/2007 |
| WO | WO-2007/073551 | | 6/2007 |
| WO | 2007/093998 A1 | | 8/2007 |
| WO | 2008/015523 A2 | | 2/2008 |
| WO | WO-2008/039449 | | 4/2008 |
| WO | WO-2008/119054 | | 10/2008 |
| WO | WO-2009/081339 | | 7/2009 |
| WO | WO-2009085466 A1 | | 7/2009 |
| WO | WO-2010/058292 | | 5/2010 |
| WO | WO-2010/082135 | | 7/2010 |
| WO | WO-2010/119340 | | 10/2010 |
| WO | WO-2010/143072 | | 12/2010 |
| WO | WO-2011/013001 | | 2/2011 |
| WO | WO-2011/024074 | | 3/2011 |
| WO | 2011/045669 A2 | | 4/2011 |

OTHER PUBLICATIONS

Examination Report Received for European Patent Application No. 06820942.8, mailed on Dec. 11, 2014, 5 pages.
Examination Report Received for European Patent Application No. 07804649.7, mailed on Feb. 17, 2015, 5 pages.
Examination Report Received for European Patent Application No. 10720818.3, mailed on Sep. 11, 2012, 3 pages.
Examination Report Received for European Patent Application No. 10785194.1, mailed on Jan. 22, 2015, 5 pages.
Examination Report Received for European Patent Application No. 11743607.1, mailed on Sep. 18, 2013, 3 pages.
Examination Report Received for European Patent Application No. 11743611.3, mailed on Dec. 19, 2014, 5 pages.
Examination Report Received for Chinese Patent Application No. 200980153997.1, mailed on Oct. 20, 2014, 8 pages. (English Translation only).
Examination Report Received for European Patent Application No. 10709054.0, mailed on Dec. 22, 2014, 4 pages.
PCT International Patent Application No. PCT/IB2010/002143, International Preliminary Report on Patentability issued on Jan. 31, 2012, 8 pages.
PCT International Patent Application No. PCT/IB2010/002265, International Preliminary Report on Patentability issued on Feb. 28, 2012, 11 pages.
200680029730.8, , "First Office Action", 200680029730.8 PRC, First Office Action, mailed on Apr. 24, 2010, 7 pages.

(56) References Cited

OTHER PUBLICATIONS

Examination Report in Chinese Patent Application No. 200980153997.1, mailed on Apr. 15, 2014, 7 pages.
Examination Report in Chinese Patent Application No. 201080011633.2, mailed on Oct. 8, 2013, 9 pages.
PCT/IB2003/005551 "International Search Report", PCT/IB2003/005551, filed on Dec. 1, 2003, by Vortman et al., International Search Report mailed Mar. 9, 2004, 3 pages.
International Application Serial No. PCT/IB2003/005551, International Written Opinion mailed on Sep. 10, 2004.
International Application Serial No. PCT/IB2004/001498, International Search Report and Written Opinion mailed on Aug. 31, 2004, 8 pages.
International Application Serial No. PCT/IB2004/001512, International Preliminary Report on Patentability mailed on Nov. 25, 2005, 5 pages.
International Application Serial No. PCT/IB2004/001512, International Search Report and Written Opinion mailed on Sep. 7, 2004, 7 pages.
International Application Serial No. PCT/IB2005/002273, International Search Report and Written Opinion mailed on Dec. 20, 2005, 6 pages.
International Application Serial No. PCT/IB2005/002413, International Search Report and Written Opinion mailed on Nov. 22, 2005, 8 pages.
International Application Serial No. PCT/IB2006/001641, International Search Report and Written Opinion mailed on Sep. 25, 2006, 8 pages.
International Application Serial No. PCT/IB2006/003300, International Search Report and Written Opinion mailed on Feb. 14, 2008, 7 pages.
International Application Serial No. PCT/IB2007/001079, International Search Report and Written Opinion mailed on Dec. 10, 2007, 11 pages.
International Application Serial No. PCT/IB2007/001079, Partial International Search Report and Written Opinion mailed on Sep. 25, 2007.
International Application Serial No. PCT/IB2007/002134, International Search Report and Written Opinion mailed on Dec. 13, 2007, 8 pages.
International Application Serial No. PCT/IB2007/002140, International Search Report and Written Opinion mailed on Dec. 29, 2008, 7 pages.
International Application Serial No. PCT/IB2008/003069, International Search Report and Written Opinion mailed on Apr. 27, 2009, 10 pages.
International Application Serial No. PCT/IB2010/000189, International Search Report and Written Opinion mailed on Jun. 1, 2010, 11 pages.
International Application Serial No. PCT/IB2010/00097, International Search Report and Written Opinion mailed on Jul. 29, 2010, 9 pages.
International Application Serial No. PCT/IB2010/002265, Partial International Search Report mailed on Mar. 11, 2011, 4 pages.
International Application Serial No. PCT/IB2011/001293, International Preliminary Report on Patentability mailed on Nov. 8, 2012, 9 pages.
International Application Serial No. PCT/IB2011/001293, International Search Report and Written Opinion mailed on Dec. 19, 2011, 12 pages.
International Application Serial No. PCT/IB2011/001375, International Search Report and Written Opinion mailed on Nov. 10, 2011, 12 pages.
International Application Serial No. PCT/IL2002/000477, International Written Opinion mailed on Feb. 25, 2003, 9 pages.
Botros et al., "A hybrid computational model for ultrasound phased-array heating in presence of strongly scattering obstacles," IEEE Trans. on Biomed. Eng., vol. 44, No. 11, pp. 1039-1050 (Nov. 1997).

Cain et al., "Concentric-ring and Sector-vortex Phased-array Applicators for Ultrasound Hperthermia," IEEE Trans. on Microwave Theory & Techniques, vol. MTT-34, No. 5, pp. 542-551 (May 1986).
Chen et al., "MR Acoustic Radiation Force Imaging: Comparison of Encoding Gradients.", 1 page, (Mar. 2007).
Cline et al., "Focused US system for MR imaging-guide tumor ablation," Radiology, v. 194, No. 3, pp. 731-737 (Mar. 1995).
Cline et al., "MR Temperature mapping of focused ultrasound surgery," Magnetic Resonance in Medicine, vol. 32, No. 6, pp. 628-636 (1994).
Cline et al., "Simultaneous magnetic resonance phase and magnitude temperature maps in muscle," Magnetic Resonance in Medicine, vol. 35, No. 3, pp. 309-315 (Mar. 1996).
Daum et al., "Design and evaluation of a feedback based phased array system for ultrasound surgery," IEEE Trans. Ultrason. Ferroelec. Freq. Control, vol. 45, No. 2, pp. 431-434 (Mar. 1998).
de Senneville et al., "Real-time adaptive methods for treatment of mobile organs by MRI-controlled high-intensity focussed Ultrasound," Magnetic Resonance in Medicine 57:319-330 (2007).
Fjield et al, "The Combined Concentric-ring and Sector-vortex Phased Array for MRI Guided Ultrasound Surgery," IEEE Trans. on Ultrasonics, Ferroelectrics and Freq. Cont., vol. 44, No. 5, pp. 1157-1167 (Sep. 1997).
Herbert et al., "Energy-based adaptive focusing of waves: application to ultrasonic transcranial therapy," 8th Intl. Symp. on Therapeutic Ultrasound., 3 pages (Sep. 2009).
Huber et al., "A New Noninvasive Approach in Breast Cancer Therapy Using Magnetic Resonance Imaging-Guided Focussed Ultrasound Surgery," Cancer Research 61, 8441-8447 (Dec. 2001).
Jolesz et al., "Integration of interventional MRI with computer-assisted surgery," J. Magnetic Resonance Imaging. 12:69-77 (2001).
Kohler et al., "Volumetric HIFU Ablation guided by multiplane MRI thermometry," 8th Intl. Symp. on Therapeutic Ultrasound, edited by E.S. Ebbini, U. of Minn. pp. 228-230 (Sep. 2009).
Kowalski et al., "Optimization of electromagnetic phased-arrays for hyperthermia via magnetic resonance temperature estimation," IEEE Trans. on Biomed. Eng., vol. 49, No. 11, pp. 1229-1241 (Nov. 2002).
Maxwell et al., "Noninvasive thrombolysis using pulsed ultrasound cavitation therapy—Histotripsy," Abstract, U.S. Natl. Lib. of Med., NIH, Ultrasound Med. Biol. (Oct. 23, 2009).
McDannold et al., "MRI evaluation of thermal ablation of tumors and focused ultrasounds," JMRI vol. 8, No. 1, pp. 91-100 (1998).
McDannold et al., "Magnetic resonance acoustic radiation force imaging," Med. Phys. vol. 35, No. 8, pp. 3748-3758 (Aug. 2008).
Medel et al., "Sonothrombolysis: An emerging modality for the management of stroke," Neurosurgery, vol. 65, No. 5, pp. 979-993 (Nov. 2009).
Mougenot et al., "MR monitoring of the near-field HIFU heating," 8th Intl. Symp. on Therapeutic Ultrasound, edited by E.S. Ebbini, U. of Minn. pp. 159-161 (Sep. 2009).
Vimeux et al., "Real-time control of focused ultrasound heating based on rapid MR thermometry," Investig. Radiology, vol. 43, No. 3, pp. 190-193 (1999).
Vykhodtseva et al., "MRI detection of the thermal effects of focused ultrasound on the brain," Ultrasound in Med. & Biol., vol. 26, No. 5, pp. 871-880 (2000).
"How is Ablatherm treatment performed?" http://www.edap-hifu.com/eng/physicians/hifu/3c_treatment_treat-description.htm, accessed Jan. 3, 2003 (3 pages).
"What is HIFU? HIFU: High Intensity Focused Ultrasound," http://www.edap-hifu.com/eng/physicians/hifu2a_hifu_overview.htm, accessed Jan. 3, 2003 (1 page).
"About HIFU, What are the physical principles?" http://www.edap-hifu.com/eng/physicians/hifu/2c_hifu_physical.htm, accessed Jan. 3, 2003 (2 pages).
"How does HIFU create a lesion?" http://www.edap-hifu.com/eng/physicians/hifu/2d_hifu_lesion.htm, accessed Jan. 3, 2003 (1 page).
"Prostate Cancer Phase I Clinical Trials Using High Intensity Focused Ultrasound (HIFU)," Focus Surgery, http://www.focus-surgery.com/PCT%20Treatment%20with%20HIFU.htm, accessed Jan. 3, 2003 (2 pages).
"Abstract" Focus Surgery, http://www.focus-surgery.com/Sanghvi.htm, accessed Jan. 3, 2003.

(56) References Cited

OTHER PUBLICATIONS

Exablate 2000 Specification, InSightec, Ltd. (2 pages) Pub 280002 (Mar. 2007).

FDA Approves Exablate 2000 as Non-invasive surgery for Fibroids, Oct. 22, 2004 (4 pages).

McGough et al., "Direct Computation of Ultrasound Phased-Array Driving Signals from a Specified Temperature Distribution for Hyperthermia," IEEE TRansactions on Biomedical Engineering, vol. 39, No. 8, pp. 825-835 (Aug. 1992).

McDonnald et al. "Usefulness of MR Imaging-Derived Thermometry and Dosimetry in Determining the Threshold for Tissue Damage INduced by Thermal Surgery in Rabbits," Radiology, vol. 216, No. 2000 pp. 517-523 (2000).

Suprijanto et al. "Displacement Correction Scheme for MR-Guided Interstitial Laser Therapy," Ellis RE, Peters TM (Eds.): MiCCAI, LNCS 2879, pp. 399-407 (2003).

Shmatukha et al. "Correction of Proton Resonance Frequencey Shift Temperature Maps for Magnetic Field Disturbances Caused by Breathing," Physics in Medicine and Biology, vol. 51, No. 18 pp. 4689-4705 (2006).

De Senneville et al., "An Optimised Multi-Baseline Approach for On-Line MR-Temperature Monitoring on Commodity Graphics Hardware," Biomedical Imaging, pp. 1513-1516 (2008).

Vigen et al., "Triggered, Navigated, Multi-Baseline Method for Proton Resonance Frequency Temperature Mapping with Respiratory Motion," Magnetic Resonance in Medicine, vol. 50, pp. 1003-1010 (2003).

International Search Report and Written Opinion mailed Sep. 7, 2011 for International Application No. PCT/IB2010/002757 (16 pages).

International Preliminary Report on Patentability for PCT/IB2010/002757 dated Apr. 17, 2012.

* cited by examiner

MAPPING ULTRASOUND TRANSDUCERS

CROSS-REFERENCE TO RELATED APPLICATION

This application is a Divisional Application of Ser. No. 12/904,655, filed Oct. 14, 2010, which claims priority to and the benefit of U.S. Provisional Patent Application No. 61/251,450, filed on Oct. 14, 2009, both of which are incorporated herein by reference.

FIELD OF THE INVENTION

The present invention relates, generally, to systems and methods for mapping ultrasound transducers. In particular, various embodiments are directed to improving the quality of the ultrasound focus using experimental feedback.

BACKGROUND

Focused ultrasound (i.e., acoustic waves having a frequency greater than about 20 kilohertz) can be used to image or therapeutically treat internal body tissues within a patient. For example, ultrasonic waves may be used to ablate tumors, eliminating the need for the patient to undergo invasive surgery. For this purpose, a piezo-ceramic transducer is placed externally to the patient, but in close proximity to the tissue to be ablated ("the target"). The transducer converts an electronic drive signal into mechanical vibrations, resulting in the emission of acoustic waves. The transducer may be shaped so that the waves converge in a focal zone. Alternatively or additionally, the transducer may be formed of a plurality of individually driven transducer elements whose phases can each be controlled independently from one another. Such a "phased-array" transducer facilitates steering the focal zone to different locations by adjusting the relative phases between the transducers. Magnetic resonance imaging (MRI) may be used to visualize the patient and target, and thereby to guide the ultrasound beam.

Figure 1:
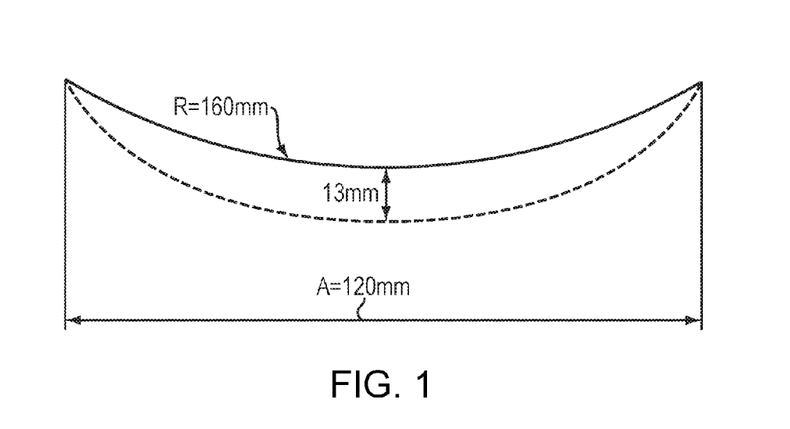
FIG. 1 is a schematic drawing illustrating the effect of a change in the transducer surface on the focus location.

The effectiveness of ultrasound therapy depends on the accuracy of the focus location, the sharpness and shape of the focal zone, and the avoidance of "hot spots" (i.e., regions of high ultrasound intensity) outside the target. Transducer elements that are not properly configured or controlled can lead to improper focus location and reduced focus quality, resulting in less effective therapy, and possibly damage to healthy tissue surrounding the target. It is therefore desirable to correct any mechanical misconfigurations. Improper transducer configuration may result from manufacturing errors, inadvertent shifting of transducer elements from their expected locations during use or repair, deformation of the transducer due to thermal expansion, or a combination of these and other effects. Even slight locational deviations can have significant effects on the quality of the transducer output. For example, as illustrated in FIG. 1, if the height of a curved transducer surface having a width of 120 mm and a nominal radius of curvature of 160 mm changes by only 1 mm, the ultrasound focus shifts by about 13 mm. In a phased array, deviations of the transducer locations from the intended locations can be compensated for by adjusting the phases with which the elements are driven. This procedure is hereinafter referred to as "mapping" the transducer.

One approach to mapping a phased-array transducer surface involves driving each transducer element individually to produce an acoustic wave pulse in water; measuring the arrival of the acoustic wave pulse in three locations using a hydrophone; determining for each location the time of flight, and thus the distance, from the transducer element; and calculating the coordinates of the element location by triangulation from the three measurements. Based on the intended and the measured actual locations of the transducer elements, the necessary phase adjustments can be calculated. This method is described in U.S. Pat. No. 7,535,794 to Prus et al., which is hereby incorporated herein by reference in its entirety. In addition to a hydrophone, implementation of the method requires other auxiliary equipment, such as an amplifier and data-acquisition module. Further, to avoid damaging the hydrophone, the mapping is typically performed at transducer power levels significantly below those used during normal operation, which can undermine the validity of the adjustments under therapeutic conditions. Alternative transducer mapping methods that do not have these drawbacks are therefore desirable.

SUMMARY

The present invention generally provides methods for mapping a phased-array transducer by generating an ultrasound focus and improving the focus quality based on experimental feedback. In various embodiments, one or more focus-affecting parameters (such as the phase and/or amplitude of one or more transducer elements) are varied, and the resulting variation of the focus quality is measured (e.g., in terms of an integral or peak intensity, focus size, or intensity profile). The focus-affecting parameter(s) are then set to values for which the focus quality is optimized. For example, the relative phases of the transducer elements may be fine-tuned one at a time to maximize the intensity at the focus. In this manner, unwanted phase shifts resulting from electronic delays or other sources may be corrected, and any deviations from the intended locations of the transducer elements may be compensated for without the need to explicitly determine the actual transducer locations.

During the mapping procedure, the ultrasound focus may be generated in a phantom. To determine the focus quality, the focus may be visualized, for example, by magnetic-resonance acoustic radiation force imaging (MR-ARFI)—an MRI technique measuring minute material displacements that are caused by and indicative of the acoustic field. The displacement increases with the acoustic field intensity. Thus, by adjusting the transducer element phases (and/or amplitudes or other focus-affecting parameters) so as to increase the material displacement in the phantom, the intensity at the focus and, consequently, the focus quality may be improved. Advantageously, MR-ARFI facilitates mapping the transducer at normal operational power levels, which increases the relevance and applicability of any mapping-based adjustments to the subsequent therapeutic operation. Further, the ultrasound focus may be imaged during the mapping procedure with the same MRI or other imaging apparatus (e.g., X-ray-based computer-aided tomography or other tomographic modality) that is used to guide the focus during therapeutic operation, and, consequently, additional (auxiliary) mapping equipment is not needed.

In one aspect, the invention provides a method for improving and/or optimizing the focus of an ultrasound transducer having a plurality of transducer elements. The method includes driving the plurality of transducer elements so as to generate an ultrasound focus, varying a focus-affecting parameter associated with one or more of the transducer elements, measuring a resulting variation on the quality of the focus, and selecting parameter value(s) that result in the best focus quality. The focus-varying parameter(s) may be or include the phase and/or amplitude of one of the transducer elements (or a group of jointly driven elements), or a phase/amplitude gradient or other parameter determining relative phase/amplitude settings of multiple transducer elements that form the whole transducer or a region thereof, or a combination of such parameters. In embodiments in which the location and/or orientation of the transducer or transducer elements are susceptible to direct user control, the focus-varying parameter(s) may, alternatively or additionally, include such location(s) and/or orientation(s). Other focus-varying parameters include, e.g., the drive frequency of the transducer. The quality measurement may involve, for instance, scanning a profile of the focus (e.g., measuring the intensity in the focus region along a line through the focus), measuring the peak (i.e., maximum) intensity of the focus, and/or measuring the integral intensity or size of the focus (i.e., integrating the intensity or area over the cross-section of the focus, where the cross-section is defined, e.g., by the regions in which the intensity is more than a set fraction, e.g., half or 1/e, of the peak intensity).

In certain embodiments, varying the focus-varying parameter(s) and measuring the resultant focus quality includes driving a selected one of the transducer elements at a variable phase while driving the other transducer elements at a constant phase (thereby varying the focus quality); determining the phase difference, if any, between the constant and variable phases where the focus quality is optimized; and, if the phase difference is non-zero, adjusting the relative phase of the selected transducer element based thereon. These steps may be repeated for the remaining transducer elements.

In some embodiments, the quality measurement comprises measuring the displacement associated with the focus using, e.g., ARFI. The ARFI measurement may involve applying a sequence of MR field gradients (such as, e.g., repeated bipolar gradients). The ultrasound focus may generated by an ultrasound pulse synchronized with the sequence of MR field gradients. The method may further involve providing a phantom (which may include a material having low tensile strength and/or a small elastic modulus), and generating the ultrasound focus and measuring the focus quality in the phantom.

In another aspect, the invention is directed to a method for mapping an ultrasound transducer comprising a plurality of transducer elements. The method includes driving the transducer elements so as to generate an ultrasound focus, and measuring a displacement associated with the focus by ARFI. Further, it involves varying the displacement by driving one of the transducer elements at a variable phase while driving the other transducer elements at a constant phase, and determining the phase difference, if any, between the constant and variable phases at which the displacement is maximized. If the phase difference is non-zero, the relative phase of the selected transducer element is adjusted based on the phase difference. The phase difference may also be used to determine the location of the selected transducer element. The application of a variable phase and determination of the phase difference between the variable and constant phases may be repeated for the remaining transducer elements. The ultrasound focus may be generated, and the displacement be measured, in a phantom, which may have a low tensile strength and/or a small elastic modulus. Acoustic-radiation force imaging to measure the displacement may involve applying a sequence of MR field gradients, e.g., a sequence including repeated bipolar gradients. The transducer elements may be driven so as to generate an ultrasound pulse synchronized with the sequence of MR field gradients.

The above-described mapping method(s) may be varied by grouping transducer elements and mapping a group, rather than an individual element, at a time. Accordingly, in yet another aspect of the invention, a selected group of transducer elements is driven at a variable phase while other groups of transducer elements are driven at a constant phase, and the phase difference between the constant and variable phases that maximizes the displacement associated with the focus may be determined and form the basis for adjusting the relative phase of the selected group of transducer elements.

In a further aspect, the invention is directed to a method for controlling an ultrasound transducer having a plurality of transducer elements. The method includes mapping the ultrasound transducer as described above by driving the transducers to generate an ultrasound focus; varying a focus-affecting parameter associated with at least one of the elements and measuring a resulting variation on a quality of the focus; and selecting a value of the parameter associated with a best focus quality. In particular, in some embodiments, mapping may include measuring a displacement associated with the focus (e.g., using ARFI), and determining, for each of the transducer elements, the relative phase associated with that element by driving the transducer element at a variable phase while driving the other transducer elements at a constant phase and determining the phase difference between the constant and variable phases that maximizes the displacement. The method further includes controlling the transducer based on the mapping step (e.g., by adjusting the relative phase of each transducer for which the phase difference is non-zero). Controlling the transducer may include driving the elements to produce outputs converging at a focus corresponding to a target treatment region. Mapping may be carried out using a phantom, and may be repeated in between therapeutic applications of ultrasound.

BRIEF DESCRIPTION OF THE DRAWINGS

The foregoing will be more readily understood from the following detailed description of the invention in conjunction with the drawings, wherein.

DETAILED DESCRIPTION

Figure 2:
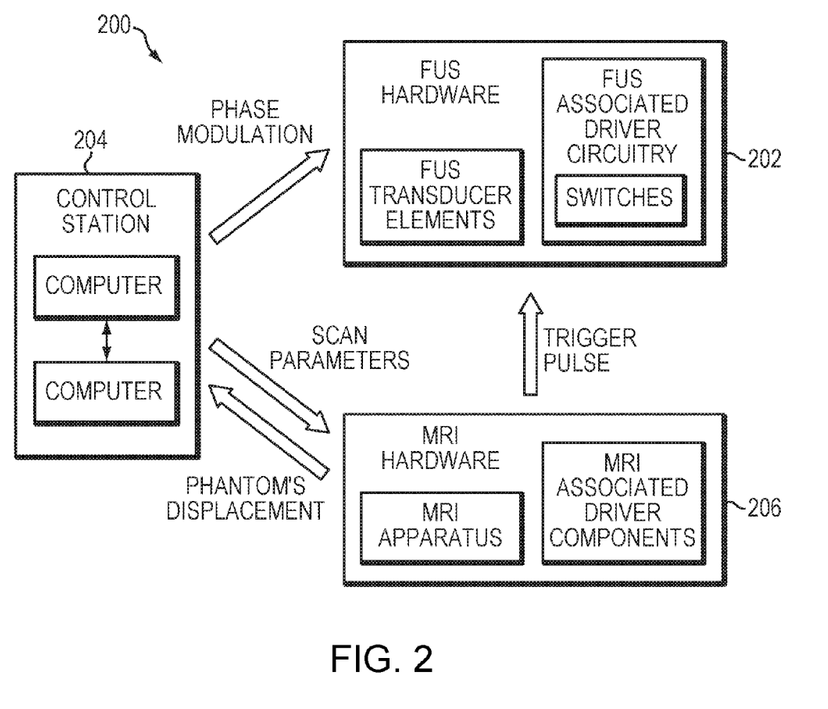
FIG. 2 is a block-diagram illustrating, on a high level, a system for performing transducer mapping in accordance with some embodiments of the invention.

FIG. 2 illustrates in block-diagram form an exemplary system for performing transducer mapping in accordance with various embodiments hereof, and the interplay between the different system components. The system includes, first, the focused ultrasound transducer hardware 202, which itself includes the transducer array, a frequency generator for providing an electronic drive signal, and drivers for the transducer elements. (As used herein, the term "transducer" refers to the entire array, as distinguished from the individual transducer elements.) Each driver contains electronic circuitry for setting the phase of the respective transducer element(s), and optionally also for adjusting the amplitude(s) of vibrations. In some embodiments, each transducer elements is independently controllable by a separate associated driver. In alternative embodiments, driver elements are organized (e.g., via hardwiring or configurable switches) into multiple groups of elements driven collectively by the same driver. The drivers are controlled by a control station 204, which may include a computer system specially designed for use with the transducer hardware, or a general-purpose computer (or cluster of computers) having suitable (and conventional) driver software installed.

The mapping system 200 further includes MRI (or other tomographic or imaging) hardware 206, i.e., an MRI apparatus and related driver components, which is likewise controlled by the control station 204. Again, control functionality for the MRI hardware 206 may be implemented in a special-purpose computer system, or in conventional driver software installed on a general-purpose computer system. The transducer hardware 202 and MRI hardware 206 may be controlled by the same computer within control station 204, or by separate computers that are in communication with one another. Further, computational functionality for processing and analyzing the images acquired with the MRI hardware 206 may be integrated with the MRI apparatus, or implemented (e.g., as a separate software module) in control station 204.

During the mapping procedure, the control station 204 sends control signals to the ultrasound transducer hardware 202 to vary one or more parameters affecting the focus properties. For example, the control station 204 may cause a phase modulation of a particular transducer element or group of elements. Further, the control station 204 provides scan parameters, or other signals triggering and/or controlling image acquisition, to the MRI or other imaging hardware 206. The relative timing of the ultrasound generation and/or modulation with respect to image acquisition may be specified in an imaging sequence, which may be programmed into the control station 204. The control station 204 may then send trigger signals to the ultrasound transducer hardware 202 and the MRI hardware 206, ensuring correct timing between the signals in accordance with the imaging sequence. Alternatively, the control station 204 may communicate a time-delay parameter, which specifies the time delay between the RF pulses and ultrasound pulses, to the MRI hardware 206, which sends a corresponding trigger pulse directly to the ultrasound transducer hardware 204.

The acquired images are processed to determine one or more parameter(s) indicative of the focus quality, which are used in the control station 204 for subsequent mapping steps. For example, in MR-ARFI-based systems, a material displacement indicative of the intensity in the focus is computationally extracted from the images, and the transducer is iteratively adjusted so as to increase the material displacement. Similarly, if thermal MRI is employed, the mapping process involves maximizing the temperature, and thus intensity, in the focus. In general, any imaging technique that provides images suitable for determining focus quality may be used. Depending on the contemplated ultrasound application, the "quality" of the focus may be expressed by different parameters. For therapeutic applications involving targeted tissue destruction, for example, the focus quality may be measured in terms of a peak intensity or total power delivered (corresponding to an integrated intensity over the focus cross section). If the target area is small, the focus size may be relevant (a smaller focus area generally corresponding to higher focus quality). In some applications (e.g., tissue heating for palliative purposes), homogeneity of the intensity focus area may be important, and focus quality may, accordingly, be measured, at least in part, by the "smoothness" of an intensity profile through the focus.

Figure 3:
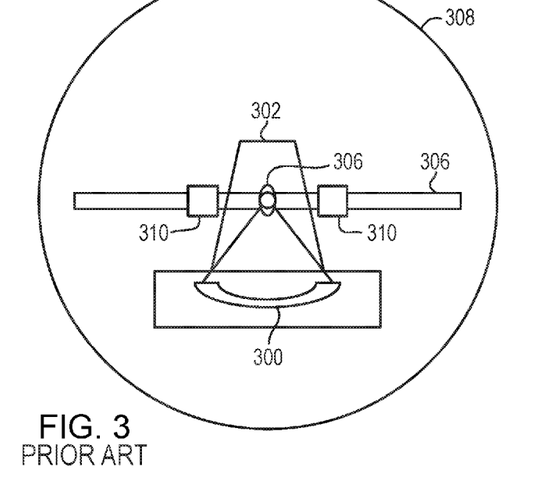
FIG. 3 a schematic diagram illustrating, in more detail, the configuration of a transducer mapping system in accordance with some embodiments.

FIG. 3 schematically illustrates an experimental setup for mapping an ultrasound transducer using tissue displacement as an indicator of focus quality. During the mapping procedure, the transducer 300 is driven so as to focus an ultrasound wave pulse into a phantom 302, which comprises or consists of a material that responds to acoustic pressure in a detectable manner. The ultrasound wave exerts acoustic radiation pressure onto the phantom material along its path. At the focus 304, where waves from the individual transducer elements converge, this pressure is highest, resulting in a temporary local displacement of the material in the longitudinal direction and/or in shear waves that propagate radially away from the focus. By using a soft phantom that responds to acoustic pressure with large enough shear strain (e.g., with a shear strain of at least $10^{-2}$), a detectable displacement field that directly reflects the acoustic field may be obtained. Suitable phantom materials have high tensile strength (e.g., higher than 100 kPa) and small elastic moduli (e.g., Young's modulus less than 1 MPa), and may include or consist of jelly-like materials such as, e.g., Silicone Gel RTV6166, provided by General Electric Co., Waterford, N.Y.

The material displacement may be visualized in an imaging plane 306 using an imaging techniques such as, e.g., magnetic-resonance-based acoustic radiation force imaging (MR-ARFI). In MR-based imaging methods, the object to be imaged (here, the phantom) is placed in a relatively uniform static magnetic field having a field strength of, typically, between about 1.5 and about 3.0 Tesla. Such a field may be generated, for example, by a large cylindrical electromagnet coil 308. The static magnetic field causes hydrogen nuclei spins to align and precess about the general direction of the magnetic field. Radio frequency (RF) pulses and magnetic gradients are then superimposed on the static magnetic field to cause some of the aligned spins to alternate between a temporary high-energy non-aligned state and the aligned state, thereby inducing an RF response signal, called the MR echo or MR response signal, in the RF antenna 310.

In MR-ARFI, transient-motion or displacement-sensitizing magnetic field gradients are applied to the phantom by gradient coils, which are part of standard MRI systems and are typically located near the cylindrical electromagnet coil 308. When the ultrasound pulse is applied in the presence of such gradients, the resulting displacement is directly encoded into the phase of the MR response signal. For example, the gradient coils and transducer may be configured such that the ultrasound pulse pushes phantom material near the focus towards regions of the magnetic field with higher field strengths. In response to the resulting change in the magnetic field, the phase of the MR response signal changes proportionally, thereby encoding in the signal the displacement caused by the ultrasound radiation pressure.

Figure 4A:
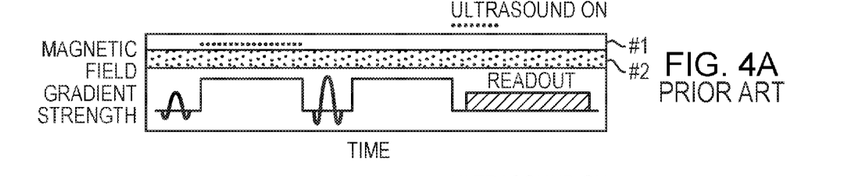
FIGS. 4A-4C illustrate various MR-ARFI sequences in accordance with some embodiments.
Figure 4B:
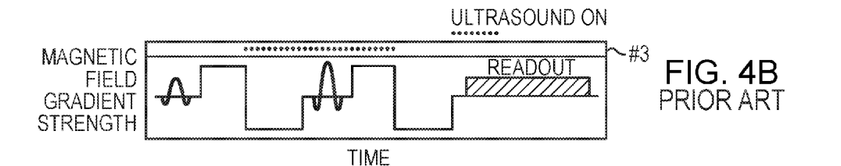
Figure 4C:
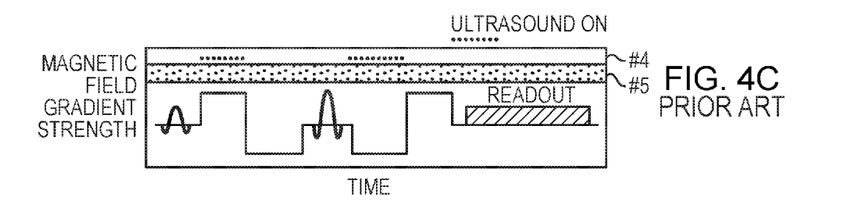

To achieve high image contrast, the ultrasound pulse, encoding gradients, and RF pulse are precisely timed with respect to each other according to a suitable displacement-encoding sequence. FIGS. 4A-4C illustrate five exemplary MR-ARFI sequences that may be used in embodiments of the invention. These sequence diagrams illustrate the order in which the displacement-encoding magnetic field gradients (thin solid lines), ultrasound pulses (dotted lines), and RF pulses (thick solid lines) appear in time. Three different field gradient sets are shown: two single lobes (a), repeated bipolars (b), and inverted bipolars (c). For gradient set (a), ultrasound may be applied during either the first or the second lobe. Similarly, for gradient set (c), ultrasound may be applied during the first or the second halves of the bipolars. In general, MR-ARFI sequences utilize magnetic field gradients that are synchronized with the ultrasound pulses. In preferred embodiments, a sequence like the repeated bipolar sequence (b) shown in FIGS. 4A-4C may be used.

Figure 5:
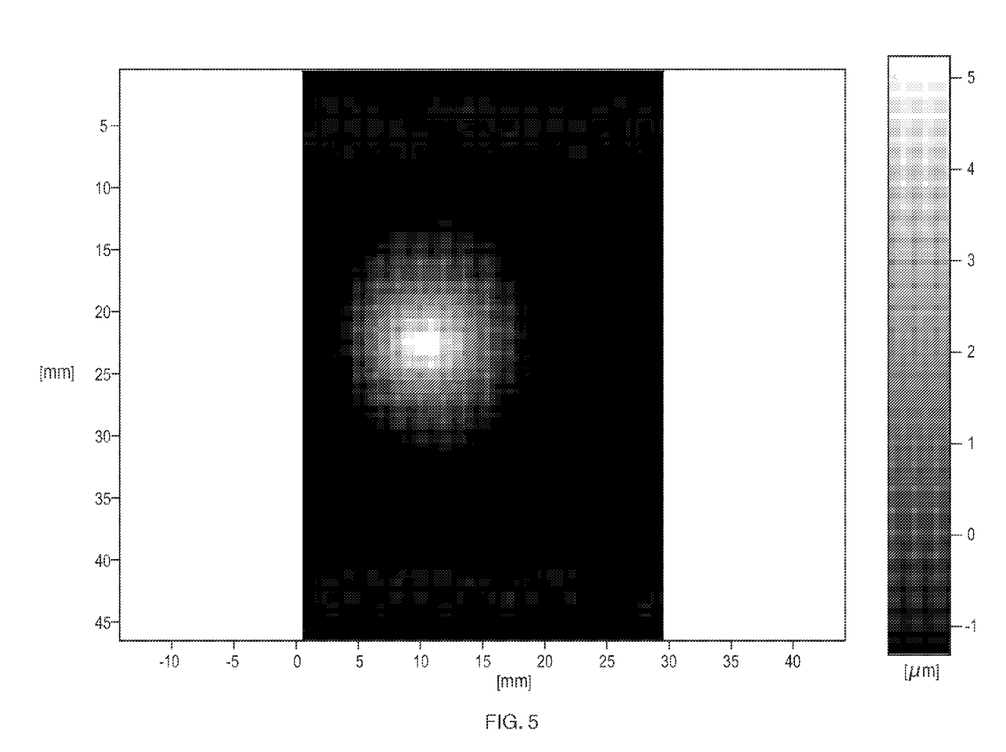
FIG. 5 is an image of material displacements in an ultrasound focus region in accordance with some embodiments.
Figure 6:
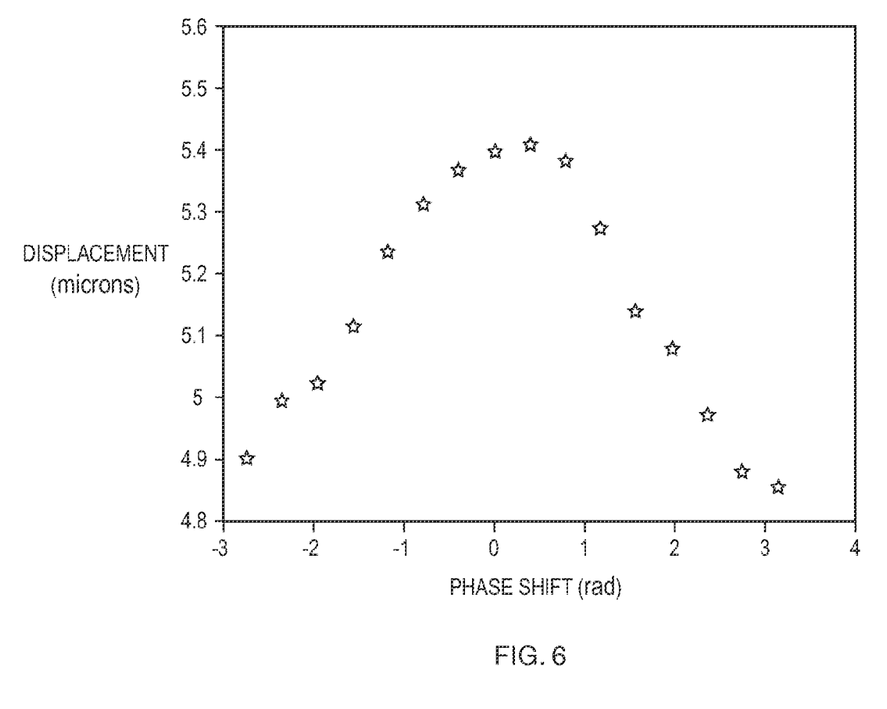
FIG. 6 is a graph illustrating material displacement in the focus center as a function of the phase of an individual transducer element, as it may be used in mapping methods in accordance with various embodiments.

An example of an MR-ARFI image of an ultrasound focus region is shown in FIG. 5. As shown, the material displacement with respect to an equilibrium position varies between about −1 μm and 5 μm, as indicated in the color-coding of the image. In general, the stronger the acoustic field intensity, the greater will be the maximum displacement at the center of the focus. The acoustic field intensity, in turn, is maximized when the elements of the ultrasound transducer emit acoustic waves that are all in phase at the focus position. If a transducer element is out of phase with respect to the others, the focus intensity in the center decreases. This relationship can be exploited to optimize the focus, and thus to map and adjust the transducer elements. Assuming, for example, that all but one of the transducer elements are properly configured, the correct phase of the last element can be determined by tuning the phase over a full cycle (e.g., between −π and +π), measuring for each phase the displacement in the focus center, and then setting the phase to the value corresponding to the maximum displacement. FIG. 6 depicts the results of such an adjustment procedure. In the illustrated example, the material displacement over the full phase cycle of one element varies between about 4.85 μm and about 5.4 μm. The maximum displacement occurs at about 0.12 rad. Consequently, the focus intensity and quality can be improved by introducing a phase shift of 0.12 rad for the tested transducer element.

In certain embodiments, mapping of the full transducer array is accomplished by varying and adjusting the phase (and/or amplitude) of each element, one at a time, while driving the remaining elements at constant phase. Typically, after each element has been mapped independently, the focus quality has significantly improved. Since the necessary phase adjustments of the transducer elements are all interrelated, however, the focus may not yet be optimal after one iteration. Therefore, in some embodiments, the procedure may be repeated iteratively. With each iteration, the phase adjustments made to maximize the displacement in the focus will, generally, decrease. Thus, a termination condition may be defined by setting a threshold value for phase adjustments, below which further adjustments are deemed immaterial or not clinically necessary. The number of iterations required to reach the termination condition may depend on the order in which the transducer elements are mapped. A mathematical algorithm, for example a "greedy algorithm" as known to persons of skill in the art, may be used to select a mapping order that results in fast convergence of the phase settings. In certain alternative embodiments, the transducer elements may be grouped, and groups of elements may be mapped simultaneously.

Figure 7:
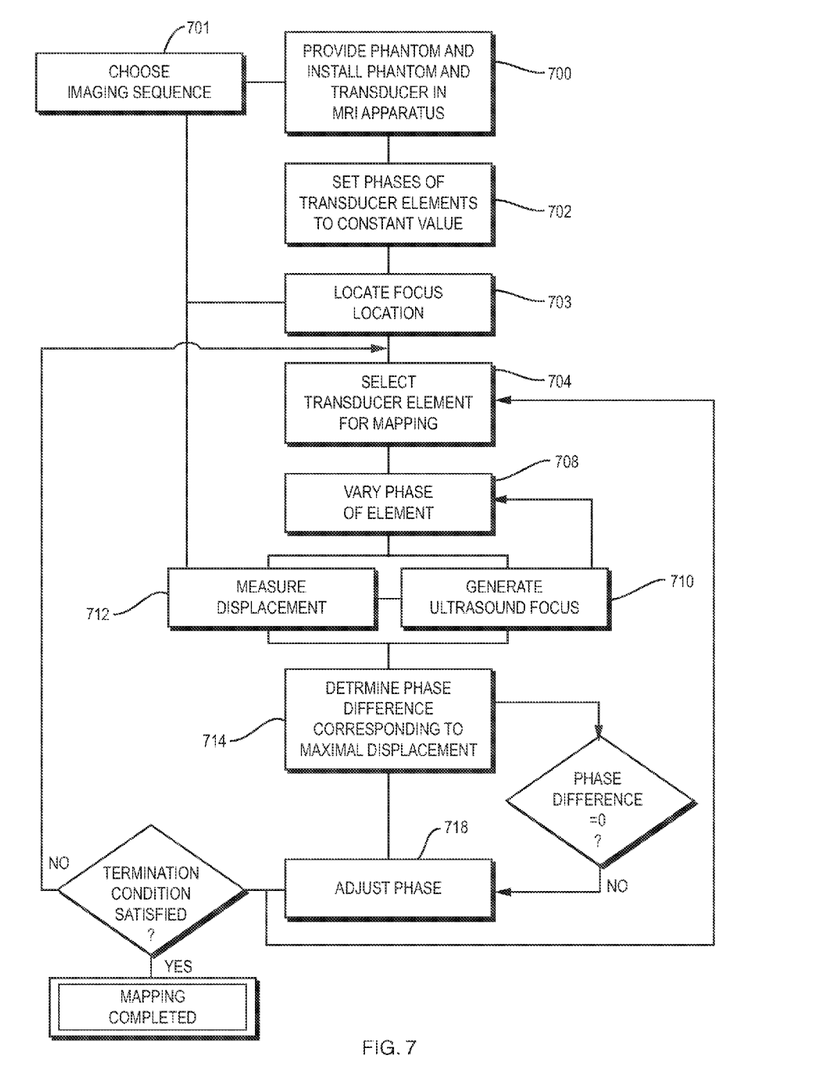
FIG. 7 is a flow chart illustrating an approach to mapping an ultrasound transducer array in accordance with various embodiments of the invention.

FIG. 7 illustrates a representative method for mapping an ultrasound transducer array in accordance with various embodiments of the invention. The method involves, in a first step 700, providing a phantom, and installing the transducer array and phantom in an MRI apparatus. Further, an imaging sequence defining the duration and relative times of ultrasound pulses, RF pulses, and encoding gradients is chosen (step 701). The phases of the transducer elements are then set to a constant value (step 702), and the focus location is determined by identifying the position of the phantom's maximal displacement in the MR-ARFI image (step 703). An iterative phase-adjustment process is subsequently started by selecting one element (or one group of elements) for mapping (step 704). The selected element is driven at a variable phase (step 708), and for each phase setting, the transducer elements are collectively driven to generate an ultrasound focus in the phantom (710). Substantially simultaneously, or after a time interval overlapping with the generation of the ultrasound focus, the displacement of phantom material in the focus region is measured by MR-ARFI in accordance with the imaging sequence (step 712). Typically, this step is repeated until the variable phase of the selected transducer element has covered a range of phases spanning an interval of 2π. In step 714, the phase difference between the constant phase and the phase of the selected transducer element that maximizes the displacement is determined (step 712). If the phase difference is non-zero, the phase of the transducer element is adjusted by this difference (step 718). Steps 704 through 718 are then repeated until each transducer element has been mapped. If the phase adjustments made in step 718 fall below a predetermined threshold value, or an alternative termination condition is satisfied, the mapping is complete. Otherwise, the mapping procedure for the array may be repeated, starting with the adjusted phase settings of the transducer elements.

The method described above may be varied in several ways. For example, the phase differences may first be determined for all the elements, without adjustments being made, and following this mapping procedure, all the phase adjustments may be made at once. In this case, an iterative phase adjustment is not needed because the reference phase, i.e., the phase of the transducer as a whole, disregarding the element under mapping, is nearly the same for all elements. Further, in some embodiments, the phases of the transducer elements may be adjusted simultaneously, rather than in succession, by varying a drive parameter affecting some or all of the elements. For example, the relative phases between transducer elements may be expressed in terms of a functional dependence of the phase on the position of a transducer element along one or two axes of the transducer array, and such functional dependence, in turn, may be characterized by one or few mathematical parameters (e.g., a linear phase gradient and/or coefficients of higher-order components of the phase modulation in one- or two-dimensional space). Rather than modulating the phase of an individual element, then, the coefficients in the functional dependence may be varied, and the corresponding effect on the focus quality observed.

Alternatively or in addition to phase variations, amplitude variations of individual elements or groups of elements (including variations of the functional dependence of the amplitude on a position along the array) may also be employed to improve the focus quality. Further, in some embodiments, the transducer elements may be movable with respect to the one another within certain ranges (e.g., as a consequence of being mounted on electronically controllable microtranslator stages, pivots, etc.). The experimental adjustment procedure described above may then be used to fine-tune the positions and/or orientations of the transducer elements. The overall shape, position, and orientation of the transducer may likewise be controllable, e.g., via clasps, movable bearings, etc.

Although the present invention has been described with reference to specific details, it is not intended that such details should be regarded as limitations upon the scope of the invention, except as and to the extent that they are included in the accompanying claims.

What is claimed is:

1. A method for mapping an ultrasound transducer comprising a plurality of transducer elements so as to improve a focus thereof, the method comprising:
   (a) driving the plurality of transducer elements so as to generate an ultrasound focus;
   (b) using acoustic radiation force imaging, measuring a displacement associated with the focus;
   (c) grouping the transducer elements;
   (d) driving a selected group of transducer elements at a variable phase while driving the other groups of transducer elements at a same constant phase, thereby varying the displacement;
   (e) determining a phase difference, if any, between the same constant phase and the variable phase where the displacement is maximized; and
   (f) if the phase difference is non-zero, adjusting a relative phase of the selected group of transducer elements based thereon.

2. The method of claim 1 further comprising scanning a profile of the focus.

3. The method of claim 1 further comprising measuring a size of a cross-section of the focus.

4. The method of claim 1 further comprising measuring an integral intensity of the focus.

5. The method of claim 1 further comprising measuring a peak intensity of the focus.

6. The method of claim 1 wherein the acoustic radiation force imaging comprises applying a sequence of MR field gradients.

7. The method of claim 6 wherein the sequence of MR field gradients comprises repeated bipolar gradients.

8. The method of claim 7 wherein step (a) comprises generating an ultrasound pulse synchronized with the sequence of MR field gradients.

9. The method of claim 1 further comprising repeating steps (d) through (f) for the remaining groups of transducer elements.

10. The method of claim 1 further comprising the step of providing a phantom, the driving step generating an ultrasound focus in the phantom and the measuring step measuring a focus quality in the phantom.

11. The method of claim 10 wherein the phantom comprises a material having low tensile strength.

12. The method of claim 11 wherein the phantom comprises a material having a small elastic modulus.

13. A system for mapping an ultrasound transducer so as to improve a focus thereof, the system comprising:
   ultrasound transducer hardware for generating an ultrasound focus, the ultrasound transducer hardware comprising an ultrasound transducer having a plurality of transducer elements and associated driver circuitry, the transducer elements being organized in multiple groups of elements;
   magnetic-resonance-imaging (MRI) hardware comprising an MRI apparatus and associated driver components for acquiring images of a region comprising the ultrasound focus; a control station in communication with the ultrasound transducer hardware and the MRI hardware, the control station being configured to
   control (i) image acquisition with the MRI hardware and (ii) generation of the ultrasound focus with the ultrasound transducer hardware in accordance with an imaging sequence that specifies the relative timing between image acquisition and ultrasound generation;
   process acquired images to determine therefrom a displacement associated with the focus;
   send control signals to the ultrasound transducer hardware to vary a phase of a selected group of transducer elements while driving the other groups of transducer elements at a same constant phase; and
   adjust the phase of the selected group of transducer elements relative to the same constant phase of the other groups based on a phase difference between the same constant phase and the variable phase where the displacement is maximized.

14. The system of claim 13, wherein the driver circuitry is hardwired to create the groups of transducer elements.

15. The system of claim 13, wherein the driver circuitry comprises switches for configuring the groups of transducer elements.

16. The system of claim 13, wherein the control station comprises separate, intercommunicating computers for controlling the ultrasound transducer hardware and the MRI hardware, respectively.

17. The system of claim 13, wherein the imaging sequence specifies a sequence of MR field gradient synchronized with ultrasound generation.

18. The system of claim 13, wherein controlling image acquisition and ultrasound-focus generation in accordance with an imaging sequence comprises sending trigger signals to the ultrasound transducer hardware and the MRI hardware.

19. The system of claim 13, wherein controlling image acquisition and ultrasound-focus generation in accordance with an imaging sequence comprises communicating a time-delay parameter to the MRI hardware, the MRI hardware being configured to send a trigger signal based on the time-delay parameter to the ultrasound transducer hardware.

20. A method for controlling an ultrasound transducer comprising a plurality of transducer elements organized into groups of elements, the method comprising:
   (a) mapping the ultrasound transducer by (i) driving the plurality of transducer elements so as to generate an ultrasound focus in a phantom, (ii) varying a focus-affecting parameter associated with at least one of the groups of elements while driving the other groups of transducer elements at a same constant value of the focus-affecting parameter and measuring a resulting variation on a quality of the ultrasound focus using magnetic-resonance acoustic radiation force imaging, and (iii) selecting a value of the focus-affecting parameter associated with a best focus quality; and
   (b) controlling the ultrasound transducer based on the mapping step so as to focus ultrasound into internal body tissue.

* * * * *